United States Patent
Wagner et al.

[11] Patent Number: 6,157,454
[45] Date of Patent: Dec. 5, 2000

[54] MINIATURE COLORIMETER

[75] Inventors: Gregg A. Wagner, Boulder; Gary Emerson, Golden, both of Colo.

[73] Assignee: Colorimeter, LLC, Glendale, Calif.

[21] Appl. No.: 09/365,193

[22] Filed: Aug. 2, 1999

Related U.S. Application Data

[60] Provisional application No. 60/098,823, Sep. 2, 1998, provisional application No. 60/098,837, Sep. 2, 1998, provisional application No. 60/098,845, Sep. 2, 1998, and provisional application No. 60/098,855, Sep. 2, 1998.

[51] Int. Cl.[7] .................................................. G01N 21/25
[52] U.S. Cl. .......................................................... 356/407
[58] Field of Search .......................... 356/407, 330–334, 356/445–448, 237.1, 402, 406, 408, 420, 425, 430, 431, 326, 328; 250/226

[56] References Cited

U.S. PATENT DOCUMENTS

| | | | |
|---|---|---|---|
| 3,986,777 | 10/1976 | Roll | 356/176 |
| 4,096,217 | 6/1978 | Roll | 264/20 |
| 4,654,794 | 3/1987 | O'Brien | 364/413 |
| 4,836,674 | 6/1989 | Lequime et al. | 356/319 |
| 5,117,101 | 5/1992 | Moore et al. | 250/226 |
| 5,383,020 | 1/1995 | Vieillefosse | 356/326 |
| 5,428,450 | 6/1995 | Vieillefosse et al. | 356/405 |
| 5,471,052 | 11/1995 | Ryczek | 250/226 |
| 5,690,486 | 11/1997 | Zigelbaum | 433/29 |
| 5,691,701 | 11/1997 | Wohlstein et al. | 340/603 |
| 5,745,229 | 4/1998 | Jung et al. | 356/73 |
| 5,759,030 | 6/1998 | Jung et al. | 433/29 |
| 5,766,006 | 6/1998 | Murljacic | 433/26 |
| 5,838,451 | 11/1998 | McCarthy | 356/406 |
| 5,844,680 | 12/1998 | Sperling | 356/303 |
| 5,851,113 | 12/1998 | Jung et al. | 433/29 |
| 5,871,351 | 2/1999 | Jung et al. | 433/29 |
| 5,883,708 | 3/1999 | Jung et al. | 356/73 |
| 5,963,333 | 10/1999 | Walowit et al. | 356/425 |
| 6,018,607 | 2/2000 | Schwarz | 385/146 |

OTHER PUBLICATIONS

X–Rite, 938 SpectroDensitometer, sales brochure (1999) 1 pg.
X–Rite, SP64 Portable Sphere Spectrophotometer, sales brochure (1999) 1 pg.

*Primary Examiner*—Frank G. Font
*Assistant Examiner*—Michael P. Stafira
*Attorney, Agent, or Firm*—Greenlee, Winner and Sullivan, P.C.

[57] ABSTRACT

The invention is a colorimeter for measurement of the color of an object. The colorimeter comprises a hand-held probe which is similar in size and shape to a large writing pen and provides the capability of measuring the color of a spot or target on, or within, the surface of an object. A measurement is made while placing the tip of the probe against, or in close proximity to, the surface of the object. The calorimeter generates from a single measurement three color data points representing the reflectance of the spot measured at the wavelengths of three primary colors. From those data points, a microprocessor can perform analyses yielding a single color value represented in various standard formats, or it can compare the measured values with a preloaded table of values. The colorimeter can then present the results on a liquid crystal display. The colorimeter contains multiple light emitting diodes (LEDs) for successively emitting light of different colors toward a target, a light sensor for receiving light reflected from the target, and a light pipe for directing light from the LEDs to the target. The display may be an integral part of the probe or contained in a separate display module connected to the probe by an electrical cable.

32 Claims, 8 Drawing Sheets

MINIATURE COLORIMETER

CROSS REFERENCE TO RELATED APPLICATIONS

This application takes priority under 35 U.S.C. § 119 (e) to U.S. provisional applications having serial numbers 60/098,823, 60/098,837, 60/098,845 and 60/098,855, all filed on Sep. 2, 1998, and all of which, along with co-pending application, attorney docket number 54–98 filed simultaneously herewith, are incorporated in their entirety by reference herein to the extent not inconsistent herewith.

FIELD OF INVENTION

This invention relates generally to devices and methods for the measurement of color and reflectance and particularly to small hand-held colorimeters.

BACKGROUND OF THE INVENTION

In many fields of endeavor, there is a need to quickly and objectively measure the color of a material or an object, or to compare the colors of different materials or objects with each other or with a reference standard. For example, in matching paint colors in automobile repair shops or in quality control of manufacturing operations.

Although there have been many devices, methods and techniques developed for this purpose, generally they have fallen into two categories: first are those which are simple and subjective and second are those which are objective but are also complex and expensive.

In the first category are the familiar color chips and charts such as found in paint stores and the like. Although simple and inexpensive, these methods are subjective in that they depend on the visual acuity and judgement of the user as well as the lighting of the environment where the color evaluation is made. Also, as a practical matter, the number of colors from which to choose is usually limited.

In the second category, there have many devices designed to objectively measure or compare colors. Those which effectively performed their functions have been complex and very expensive. Many are large laboratory instruments having separate bulky or bench-mounted components. Others are smaller self-contained units but which contain high-precision optical components and complex electronic circuitry for performing sophisticated color spectrum analysis. The following inventions are briefly described as examples of the second category, U.S. Pat. No. 5,838,451 discloses an apparatus for the measurement of spectral reflectance or spectral absorbance of an object or a material. The reflectance apparatus comprises multiple LEDs surrounding a photosensor, all mounted on a common substrate, and a lens for coupling light to and from the object.

U.S. Pat. No. 5,844,680 also discloses apparatus for measuring and analyzing spectral radiation. It discloses three embodiments comprising: (1) multiple LED light sources with a single sensor, (2) a single light source with multiple sensors, and (3) multiple sources and sensors. In each case the wavelength spectra of the multiple sources or sensors overlap to provide full spectrum color measurement within the range of interest.

U.S. Pat. No. 5,851,113 discloses a system comprising a probe containing a plurality of optical fibers connected to a color measurement system. The patent describes various means of color measurement, including multicolored light sources (RGB), and various analysis techniques.

U.S. Pat. No. 5,690,486 discloses a lightweight, handheld, battery powered device for detecting tooth colors. The device comprises a main body, which includes device electronics, and a wand comprising a fiberoptic bundle for placing against the tooth. The main body contains three LED's providing three primary colors (RGB) and a photo detector all optically coupled through the fiber optics wand to its tip.

U.S. Pat. No. 5,691,701 describes a system using multicolored LEDs for sensing the color of a gas, fluid or vapor. The system uses fiber optics for coupling light to and from the gas, fluid or vapor.

Each of the preceding examples describes technology, apparatus or methods for making color measurements or comparisons. However, none of them describes the invention of a small, hand-held and inexpensive calorimeter which can permit an operator unskilled in color analysis to quickly and objectively make consistent color measurements and comparisons.

It is advantageous for such a colorimeter to be compact, inexpensive, and versatile. Versatility is enhanced by the use of designs that avoid specular reflection from glossy or irregular surfaces. It is advantageous for a calorimeter to include an easy-to-use display or other interface so that users with little training can take measurements. It is also advantageous for the user interface to display information in a non-numerical format, so that the user can more readily convey the necessary information verbally.

It is therefore an object of the invention to provide a small and inexpensive apparatus using simple procedures for measuring the color of an object.

BRIEF SUMMARY OF THE INVENTION

The invention is a colorimeter for measuring the color of an object. The colorimeter comprises a hand-held probe which is similar in size and shape to a large writing pen. In a first embodiment, the entire calorimeter is contained within the probe and an integral display panel. In a second embodiment, the colorimeter is contained within the probe and a separate display module which is connected to the probe by an electrical cable.

The calorimeter provides the capability of measuring the color of a spot, hereinafter referred to as a target, on the surface of an object. A measurement is made while placing the tip of the probe against, or in close proximity to, the surface of the object. Although the measurement is made at the surface of an object, the color being measured may be inside the surface as in the case of pigment within a transparent or translucent material. The colorimeter generates from a single measurement three color data points representing the reflectance of the target measured at the wavelengths of three primary colors. From those data points, a microprocessor within the colorimeter can perform analyses yielding a single color value represented in various formats, such as RGB or tristimulus values, or it can compare the measured values with a preloaded table of values. The colorimeter can then present the results on a display.

As used herein, the term "color value" means any representation of a measured color. For example, it can be a single number or a symbol, or it can be a group of numbers or symbols such as three RGB ratios or a set of tristimulus values. A color value can also be represented by the result of a comparison of measured color values to stored color values.

The colorimeter comprises a probe tip containing multiple light emitting diodes (LEDs) for successively emitting light of different colors toward a target, a light sensor for receiving light reflected from the target, and a light pipe for directing light from the LEDs to the target, all within the probe itself.

The LEDs surround the light sensor preferably in a circular arrangement within the probe tip. Light is conducted from the LEDs to the target via the solid portion of a hollow light pipe. The LEDs preferably emit three primary colors. The three colors are preferably red, green and blue (RGB) and are preferably discrete in the sense that their wavelengths do not overlap. One or more LEDs of each color may be used depending on the efficiency of the LEDs of different colors and the level of illumination required.

The LEDs are embedded in, or abutted to, the proximal end of a hollow semi-conical light pipe extending substantially from a substrate supporting the LEDs to the distal end of the probe tip. An opaque axial bore extends through the light pipe from near the probe tip to the light sensor. The bore provides a path for reflected light to reach the sensor and shields the sensor from direct light from the LEDs.

The sensor is a relatively broad-spectrum device which is sensitive to all the wavelengths emitted by the LEDS. In operation, the LEDs are illuminated sequentially by color and the light of each color reflected from the target is sensed by the light sensor and represented by an analog electrical signal. The analog signal obtained from each color is converted to a digital signal whose value is then stored for analysis with the other color values.

In the a first embodiment, referred to herein as the calorimeter, the probe contains the electronic circuitry for interfacing to the optical devices and for digitizing, storing and analyzing the reflected light signals. The probe includes an integral display panel, preferably a liquid crystal display (LCD), and associated circuitry for displaying the results of the measurements or comparisons. It also includes the batteries for providing power and a button or switch for initiating a measurement.

In a second embodiment, referred to herein as the modular calorimeter, the probe contains the electronic circuitry for interfacing to the optical devices and for digitizing the reflected light signals as well as the switch for initiating the measurements. However, in this embodiment, the display panel and the electronic circuitry for analyzing the reflected light signals are located in a separate display module connected to the probe by an electrical cable. In this embodiment the display module includes the batteries for providing power and additional menu buttons or switches for controlling the functions of the colorimeter.

DETAILED DESCRIPTION OF THE INVENTION

In the drawings, like reference numerals indicate like features; and, a reference numeral appearing in more than one figure refers to the same element. The drawings and the following detailed descriptions show specific embodiments of the invention. Numerous specific details including materials, dimensions, and products are provided to illustrate the invention and to provide a more thorough understanding of the invention. However, it will be obvious to one skilled in the art that the present invention may be practiced without these specific details.

Figure 1:
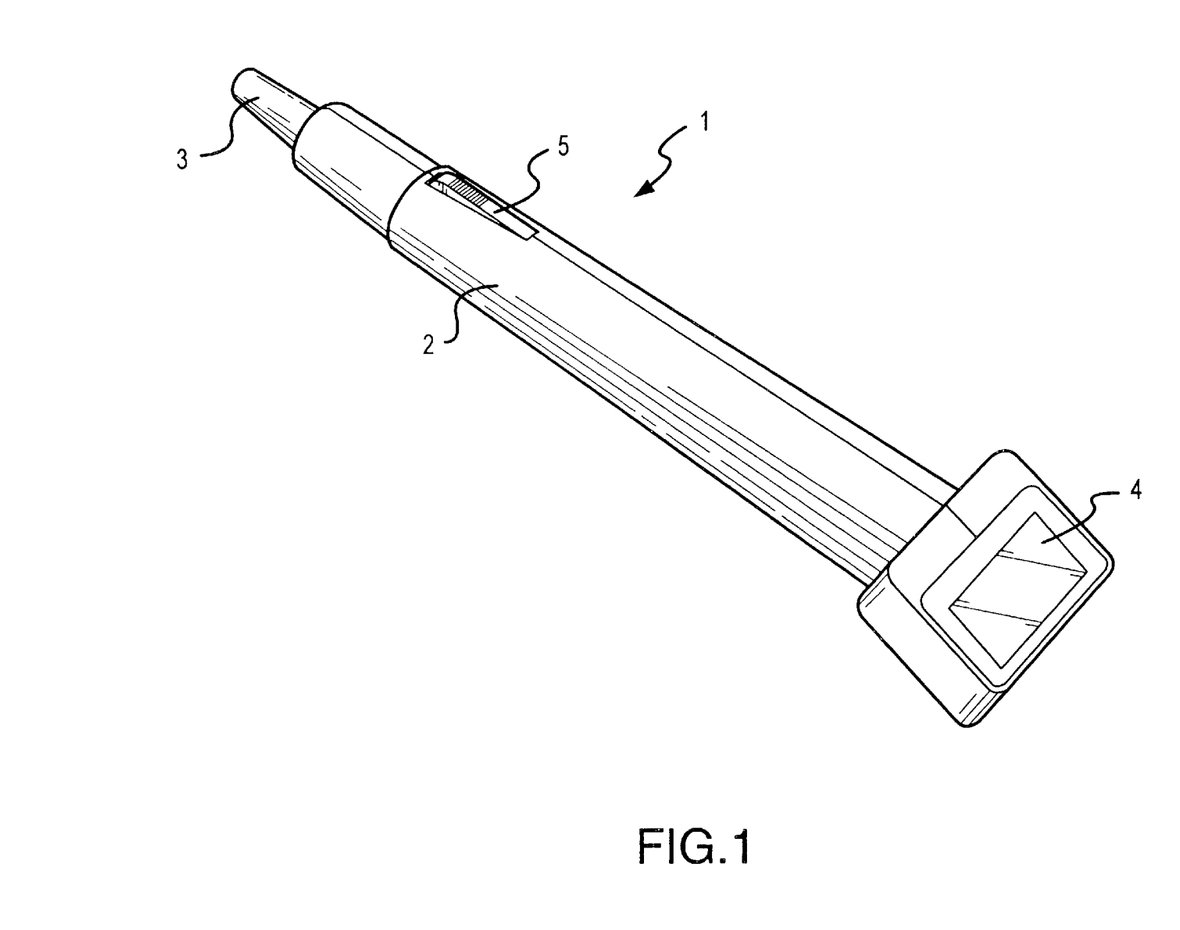
FIG. 1 is a drawing showing the exterior of the calorimeter.

An exterior view of the invention is shown in FIG. 1. The calorimeter 1 comprises probe body 2, probe tip 3, display panel 4 and measure button 5.

Figure 2A:
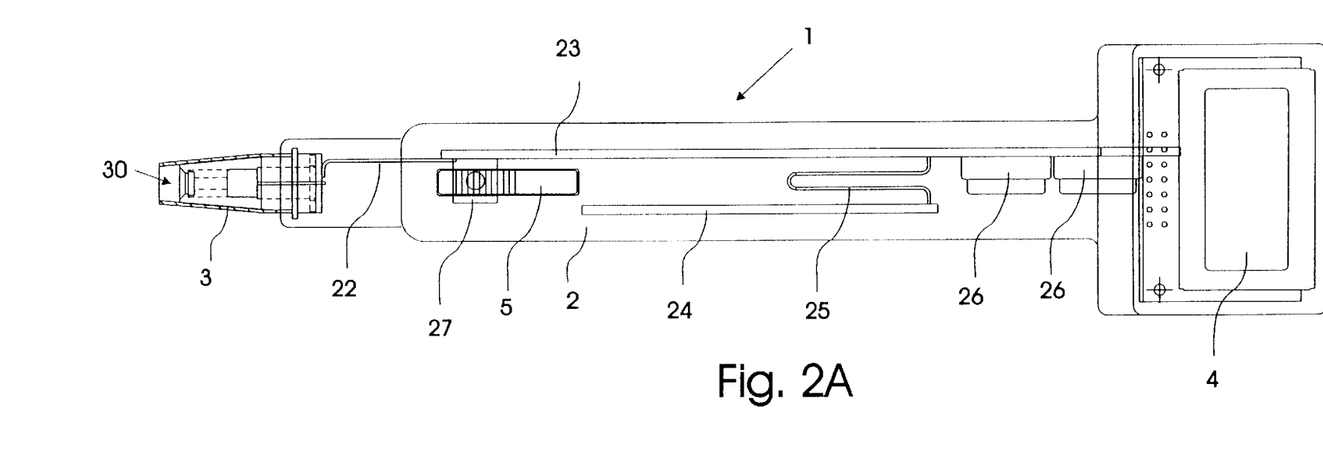
FIGS. 2A and 2B are cross sectional views of the calorimeter.
Figure 2B:
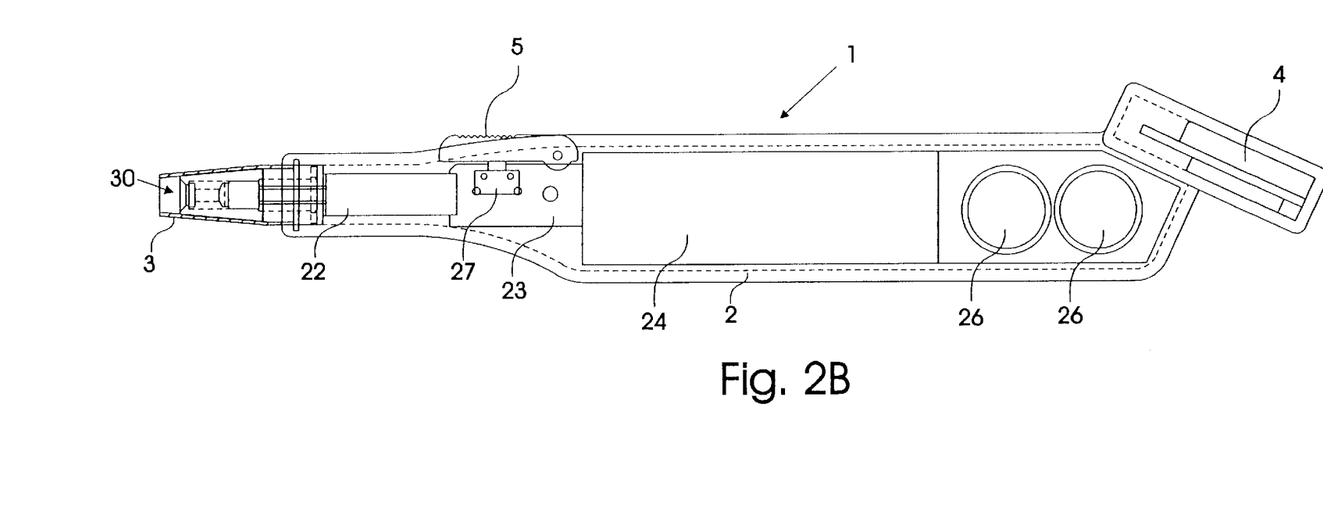

FIGS. 2A and 2B are cross sectional top and side views, respectively, of the calorimeter. The colorimeter 1 comprises body 2, probe tip 3, display panel 4, measure button 5, optics assembly 30, optics circuit ribbon 22, analog circuit board 23, digital circuit board 24, interconnect circuit ribbon 25, measure switch 27 and batteries 26.

Figure 3:
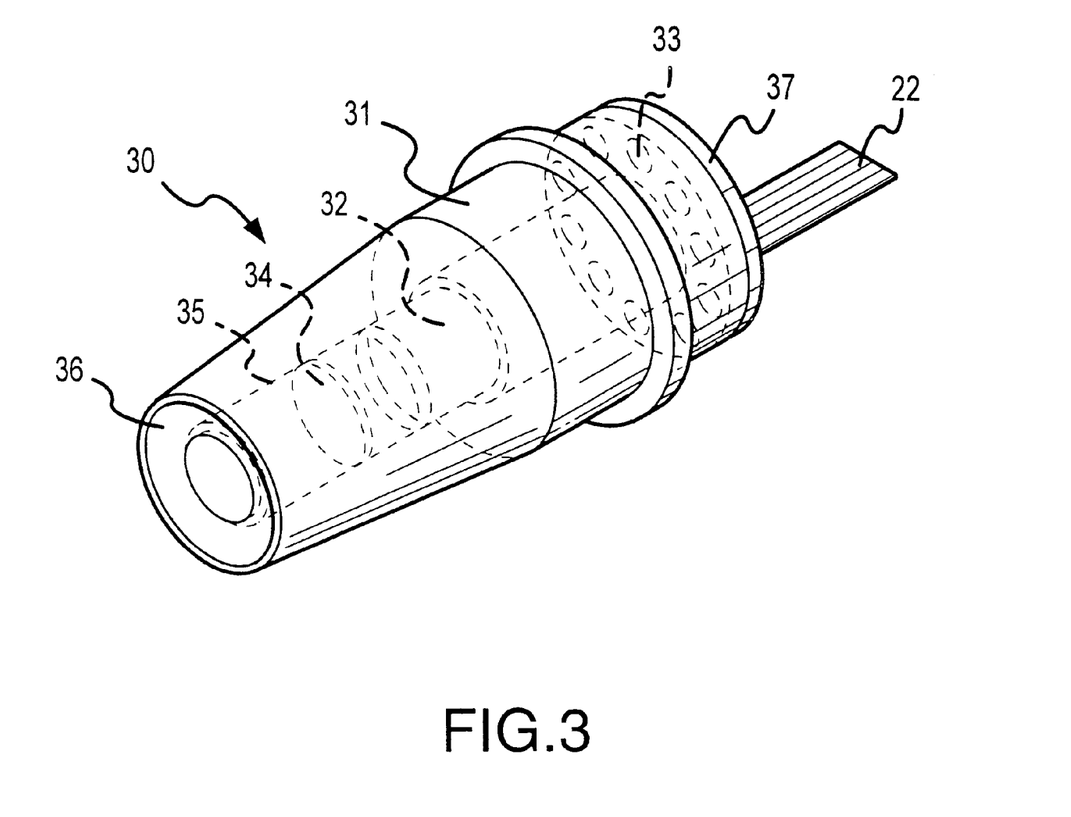
FIG. 3 s a perspective drawing of the optical assembly.

FIG. 3 is a drawing of the optics assembly. Optics assembly 30 is enclosed within probe tip 3 and comprises light pipe 31, light sensor 32, LEDs 33 and optical filter 34. Light pipe 31 has the shape of a truncated cone with a concentric opaque bore 35 and an illumination surface 36 on its distal end. Light sensor 32 and filter 34 are fitted into bore 35. LEDs 33 are abutted to, or imbedded in, the proximal end of light pipe 31. LEDs 33 and light sensor 32 are electrically connected to optics circuit board 37 which is in turn connected to optics circuit ribbon 22. Illumination surface 36 preferably has a truncated cone shape which may be concave (i.e., with its smaller end toward its proximal end) with a diffusing surface finish or which may be convex (i.e., with its smaller end toward its distal end) with a smooth refracting surface. However, surface 36 may have a diffusing or refracting surface of any shape which provides adequate illumination of the target. The outer conical surface of assembly 30 may be coated, or separated from the interior surface of tip 3, to satisfy the index of refraction requirements for light pipe operation.

Light emitted from LEDs 33 is contained within light pipe 31 by total internal reflection (TIR) and guided through illumination surface 36 to illuminate the target. If surface 36 is a diffusing surface, light is scattered uniformly over the target. If surface 36 is a refracting surface, light is refracted onto the target. The cone angle and surface finish of surface 36 can be chosen by one of ordinary skill in the art to optimize the uniformity and intensity of the illumination of the target. Probe tip 3 shields the target from external ambient light. Light reflected from the target passes through bore 35 and filter 34 to sensor 32. The length and diameter of bore 35 are chosen to prevent specular reflections from the target from reaching sensor 32. The surface of bore 35 may be coated to prevent light from the LEDs from reaching sensor 32. Filter 34 may be optionally used to pass only the desired wavelengths and to block light having other wavelengths. For example, filter 34 may be a bandpass filter which blocks infrared and ultraviolet light or it may comprise one or more notch filters used to provide separation between the wavelengths emitted by different color LEDs. A notch filter is a filter which blocks light of a narrow band of wavelengths.

The probe tip comprises a sleeve that is sufficiently flexible and conformable to facilitate tight contact with the target surface. Opaque materials are preferred for this purpose (e.g., an opaque vinyl or rubber), sufficiently flexible and conformable to facilitate fairly tight contact with the target surface. Preferably, the sleeve is sufficiently flexible to conform to an irregular surface. In medical or dental applications, the sleeve should be sanitary and disposable. A suitably-designed sleeve is preferably stiff enough to control the target position relative to the light sources and sensor. The probe tip can be removable or interchangeable with tip shapes customized for particular targets.

In operation, the probe tip is placed against the target and the LEDs of each color are illuminated in sequence. As the target is illuminated by each color, a portion of the reflected light is captured by the sensor which produces an analog electrical signal representing the intensity of the reflected light.

Figure 4:
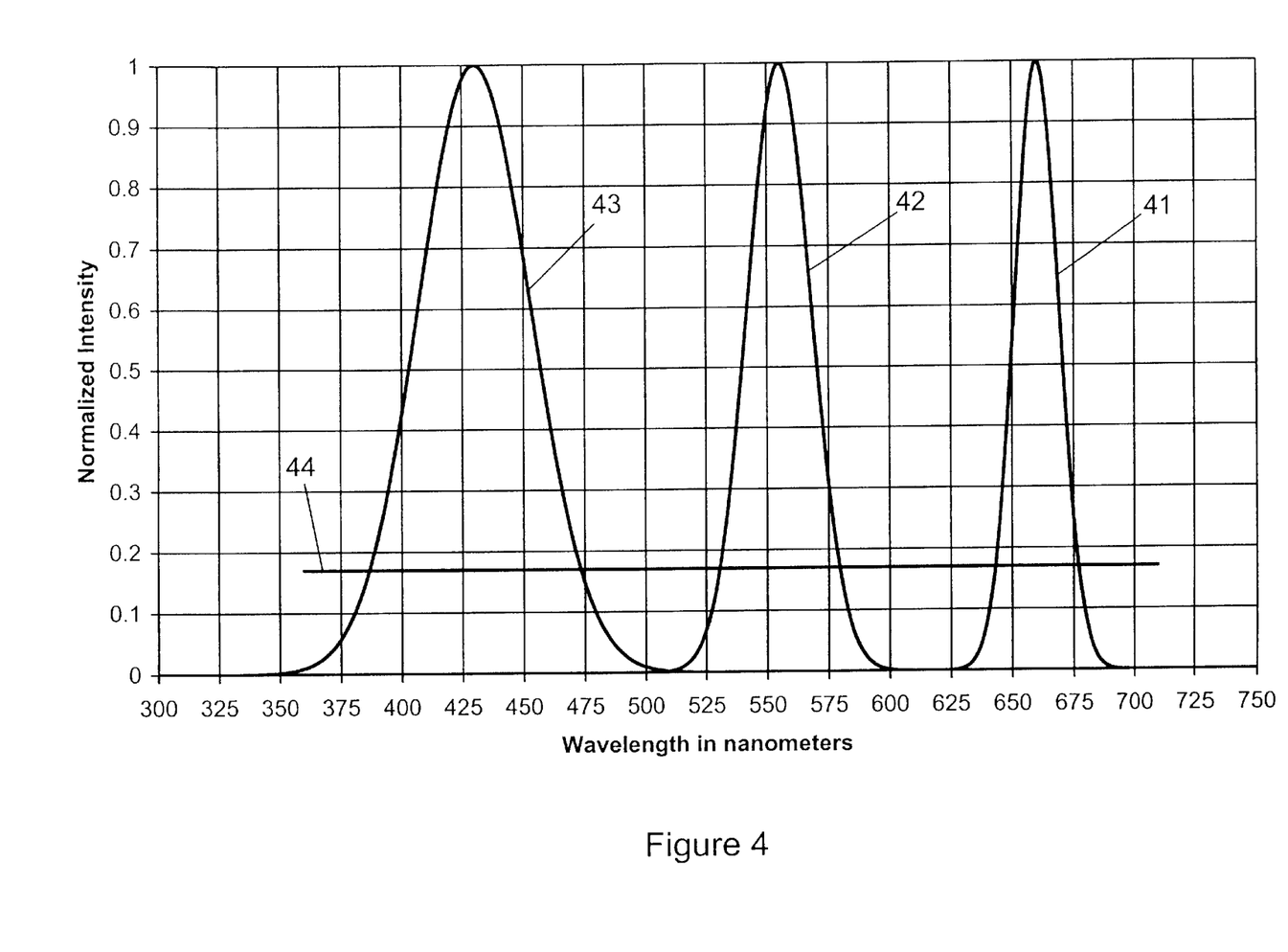
FIG. 4 is a plot of light intensity vs. wavelength for the illumination system.

An exemplary plot of light intensity vs. wavelength for three LED colors is shown in FIG. 4. This example shows spectral profiles for a red LED 41, a green LED 42 and a blue LED 43. In this plot, the three profiles are discreet; that is, they do not overlap. However, as known to those skilled in the art, LEDs having profiles with different peak wavelengths and different widths may be used. Also, the inherent emission profiles of the LEDs may be altered by optical filters or coatings on the LED encapsulations. The effective profile widths can be altered by the use of optical notch filters in the sensor light path or by setting a detection threshold 44 either within the signal path from the sensor to the microprocessor or in the digital processing routines of the microprocessor. Such a threshold can be set to disregard light intensities below the threshold and thereby eliminate wavelengths outside the threshold. A different threshold can be specified for each color and stored in memory. The stored threshold values can be used directly by the microprocessor or converted by a digital-to-analog converter (DAC) to an analog signal for use by a comparator in the analog signal path.

Figure 5:
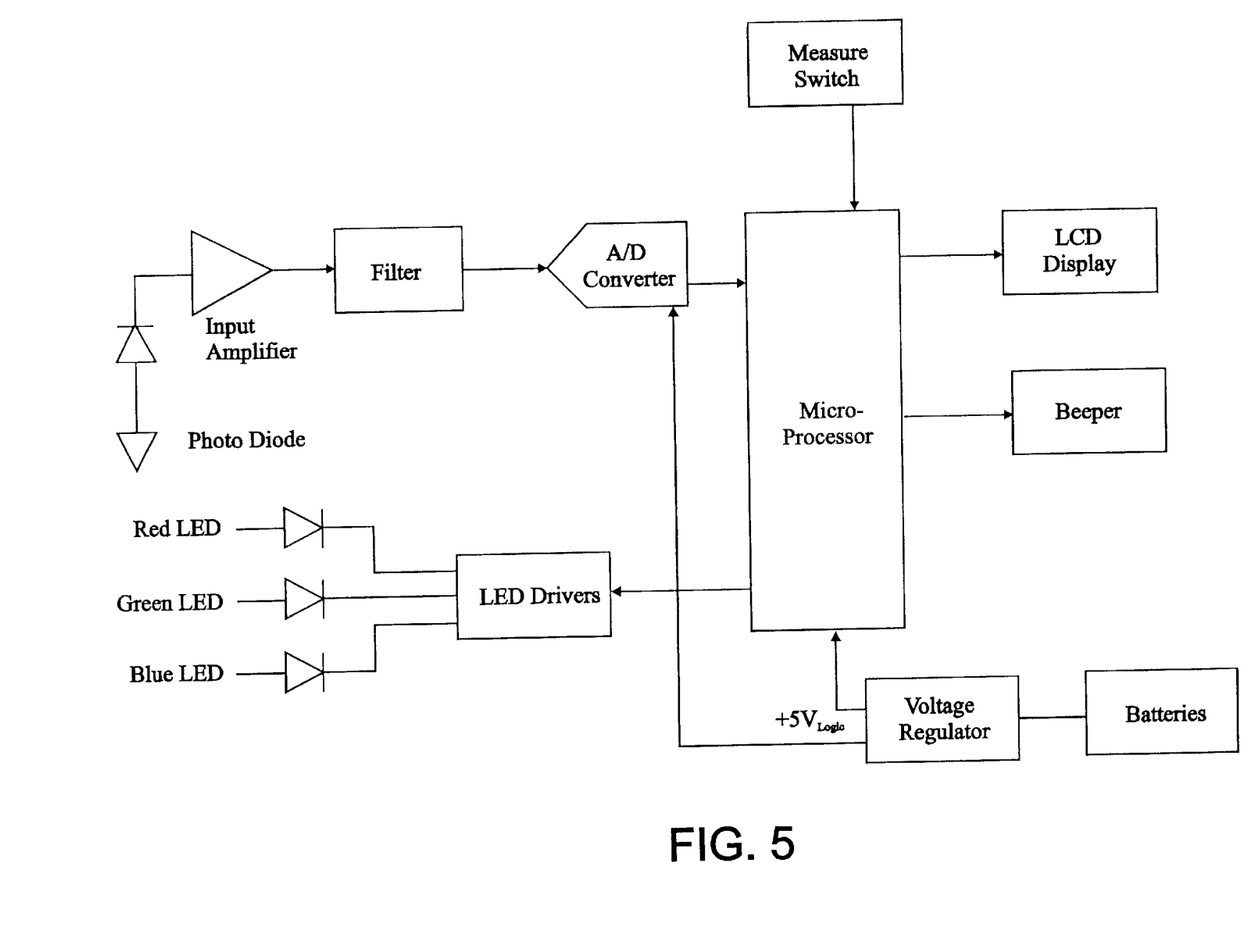
FIG. 5 is a block diagram of the circuits in the calorimeter.

A block diagram of the circuits contained in the colorimeter is shown in FIG. 5. Although the circuits are shown as separate functional blocks, it will be recognized by those with ordinary skill in the art that some or all of the functions can be combined in integrated circuits. The term microprocessor as used herein includes the family of devices known as microcontrollers.

To compensate for variations in sensitivity of the sensor across the wavelength spectrum and for differences in the efficiency of the different LEDS, the light output of each of the LEDs may be adjusted by varying its current.

Current is preferably supplied to the LEDs in short pulses to minimize self-heating and the resulting change in light-generating efficiency. If necessary to enhance accuracy within a measurement, multiple short pulses can be used to make a number of measurements and the results averaged, or otherwise statistically analyzed, to produce a single result.

Each time the calorimeter is turned on, and prior to its operation, a calibration sequence is performed. This consists of measuring the known reflectance of a substantially white reference surface using all the colors in the probe. Preferably, white (and black, if used) calibration reference surfaces have a very low gloss (i.e., reflecting more than 100 times more light energy diffusely than specularly at the wavelengths to be measured).

The operation of the calorimeter is initiated by pressing the probe tip against the surface to be measured and pressing the "measure" button. This action is detected by the microprocessor and the measurement sequence is initiated.

The measurement sequence comprises simultaneously sending a short current pulse to each of the LEDs of one color to illuminate the target. Reflected light from the target is detected by the sensor which converts the light to an analog electrical signal. The analog signal is coupled to an analog-to-digital converter (ADC) that converts the analog signal into a digital signal whose value is then stored in the storage device. This process is repeated for each of the colors in the system.

Prior to making a color measurement, the calorimeter is calibrated by performing the measurement sequence on a white reference. In some applications, the calibration may include a black or dark reference as well. All the color values measured for the reference surface are stored in memory as reference (i.e., calibration) values.

When color measurements are made, the microprocessor retrieves the stored reference values uses them to compute the ratio of the measured value to the reference value for each color.

As used herein, a color ratio is defined as the ratio of the intensity of the light reflected onto the sensor from a target, whose color is being measured, to the intensity of the light reflected onto the sensor from the white calibration reference. When a black (or dark) reference is used, the color ratio is the ratio of the target intensity to the difference in intensity between the white and black (or dark) references. A color ratio is preferably generated for each LED color used in the measurement.

The measured ratios can then be compared with stored ratios in a look-up table. When a close match is found its identification can be shown on the display.

When the calorimeter is first turned on, it performs a self-diagnostic test to ensure proper operating function. After the completion of a successful diagnostic test, the user is directed to calibrate the calorimeter.

Upon completion of the calibration step, the calorimeter is ready to perform a measurement.

Figure 6:
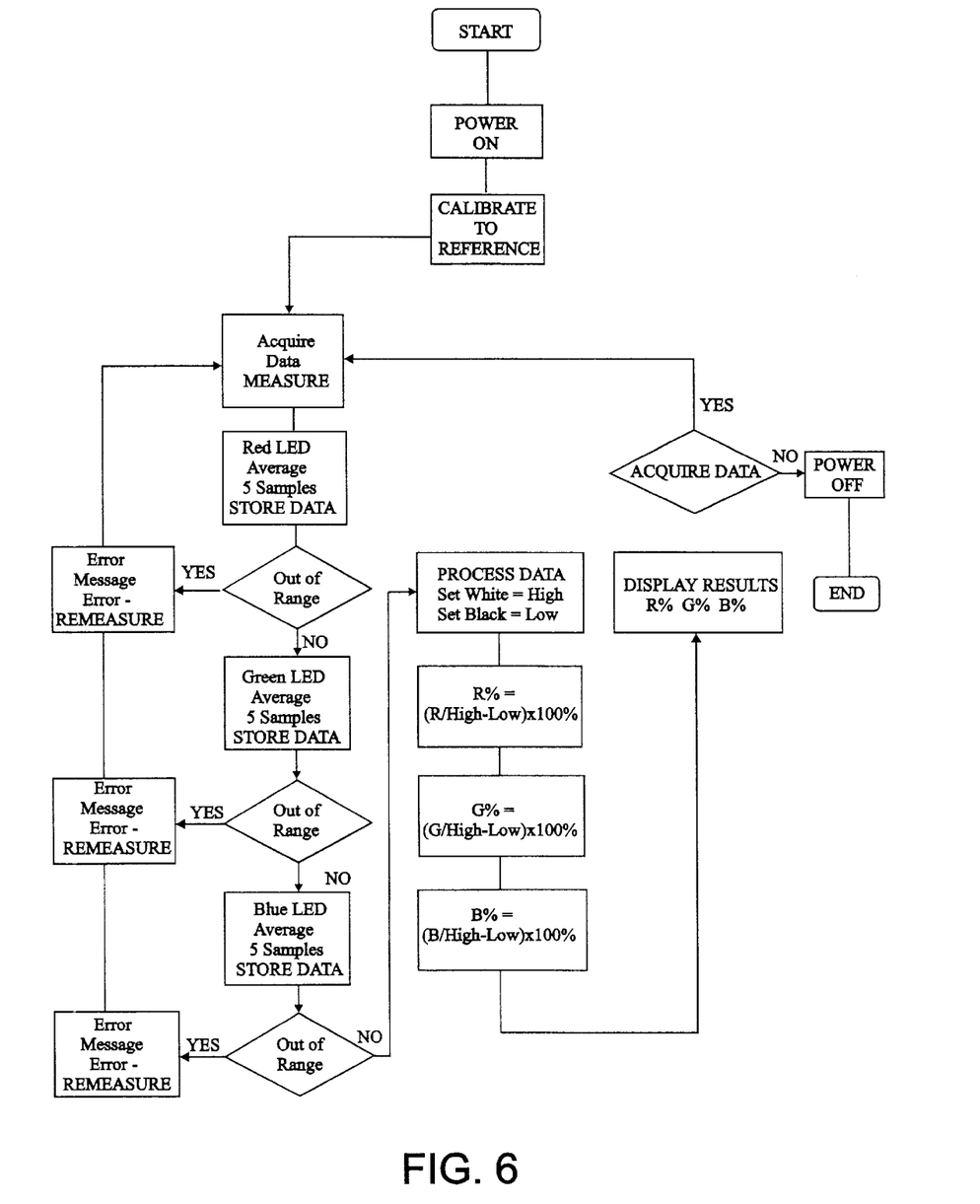
FIG. 6 is a state diagram for the calorimeter operating system.

FIG. 6 is a flowchart of the software executed during the measurement process. The calorimeter measures, processes, stores and displays reflectance measurements of red, green, and blue as shown. In some applications, these values are compared to those in a comparison look-up table stored in the colorimeter's memory. When the values match within the range of a stored color code number, the color code number is displayed on the display.

A sequence for color measurement using the calorimeter is:

At the start of operation, the colorimeter is switched on by a power switch or, alternatively, by pressing the measure switch.

When first turned on, the colorimeter prompts the user to calibrate using a white reference and optionally either a black reference or a dark measurement. The user applies the probe tip to the white reference, then depresses the "measure" button. An "end of measurement" beeper can be provided to indicate the end of a measurement operation. Optionally, this step may be repeated to calibrate to a black reference. The calibration data is stored in the calorimeter until the unit power is turned off, and is used in calculation of measured color values. This calibration sequence occurs each time the unit is turned on.

After calibration, measurements are made by placing the probe against the target and depressing the "measure" button. Each time the "measure" button is depressed, the colorimeter will take a reflected light intensity measurement for each color, process it, and indicate the end of the measurement. The color value is then calculated and displayed on the display panel. Preferably, each measurement comprises a number of short measurements taken in rapid succession and statistically analyzed during processing of the data to produce a single measurement value.

A measurement is repeated each time the "measure" button is activated. Each new measurement is displayed on the display panel, overriding the previous measurement.

After use, the calorimeter may be switched off or, alternatively, controls can be provided in the hardware and software to allow the colorimeter to time out and turn itself off.

Figure 7:
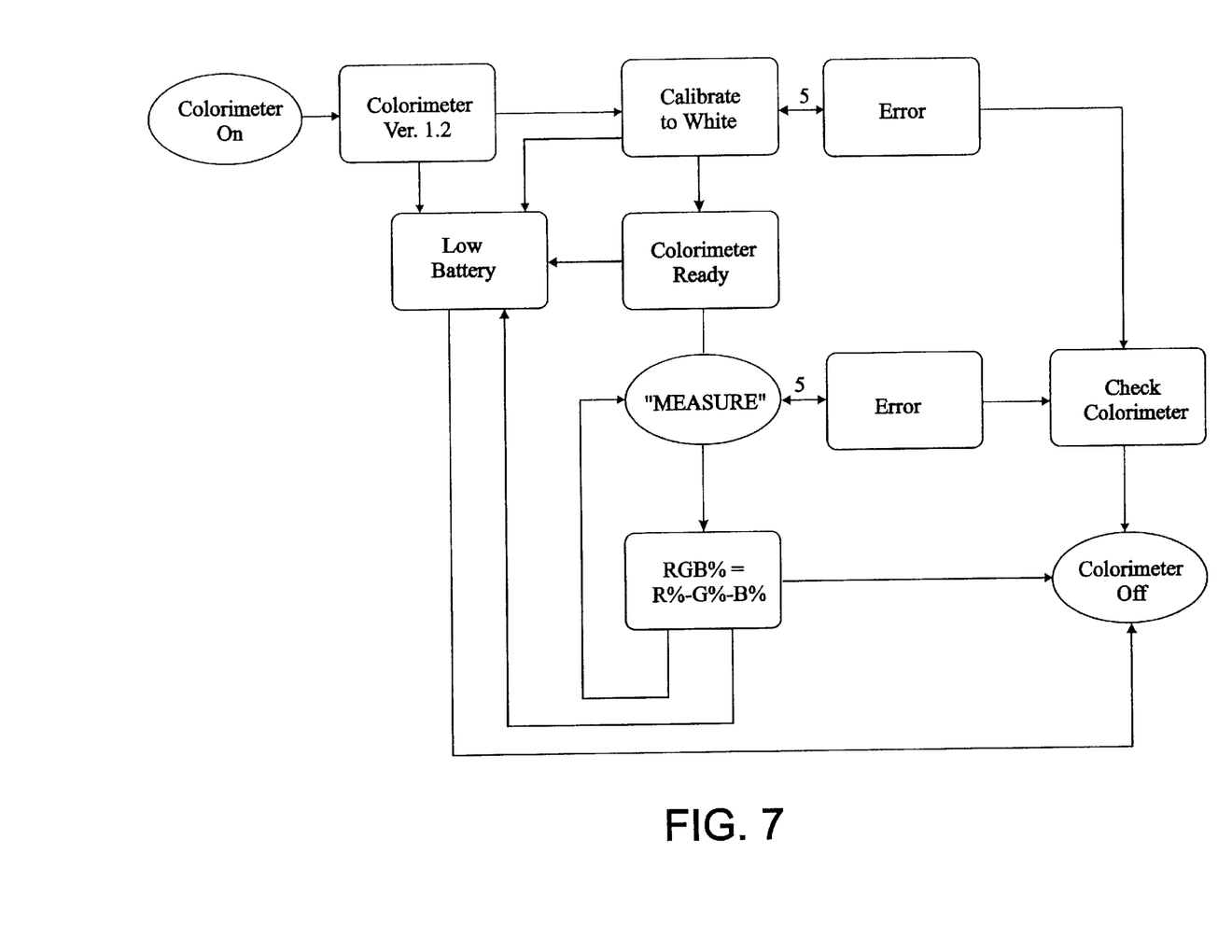
FIG. 7 is a flow chart for the colorimeter operating system.

FIG. 7 is an exemplary state diagram of images that can be presented to an operator by the display panel of the invention. In the diagram, rectangles indicate displays and ovals indicate user inputs.

A predetermined combination of LED's can be used to illuminate each of the reference samples and the resulting measurements stored. Then these measurements can be used in two ways. First, the measurements from the white reference sample can be used to set "out of range" or error limits. If excessive ambient light leaks into the colorimeter, for example, the measurement could exceed the error limit. It could also indicate that one of the LED's is positioned to allow undesired specular reflection to enter the sensor aperture. A second function of the measurements could be to allow computation of light intensity. Under normal measurement conditions, the sensor should return a signal between that of the white and the black references; however, if the probe is pointed toward an external light source, the signal could far exceed the level measured for the white reference. Such abnormal signal levels can be used to indicate error conditions.

For reliable readings of irregular samples, the software can calculate various combinations or sequences of strobed LED's, using a selection process for choosing the most reliable measurement. For example, several combinations of LED's can be strobed, measurements recorded, and medians determined. Upward aberrations may be caused by a high degree of specular reflection in the measurement. Downward aberrations may be caused by irregular surfaces preventing adequate reflection, or perhaps a degraded LED. Such aberrations may be discarded or identified by a suitable process, preferably in software.

Figure 8:
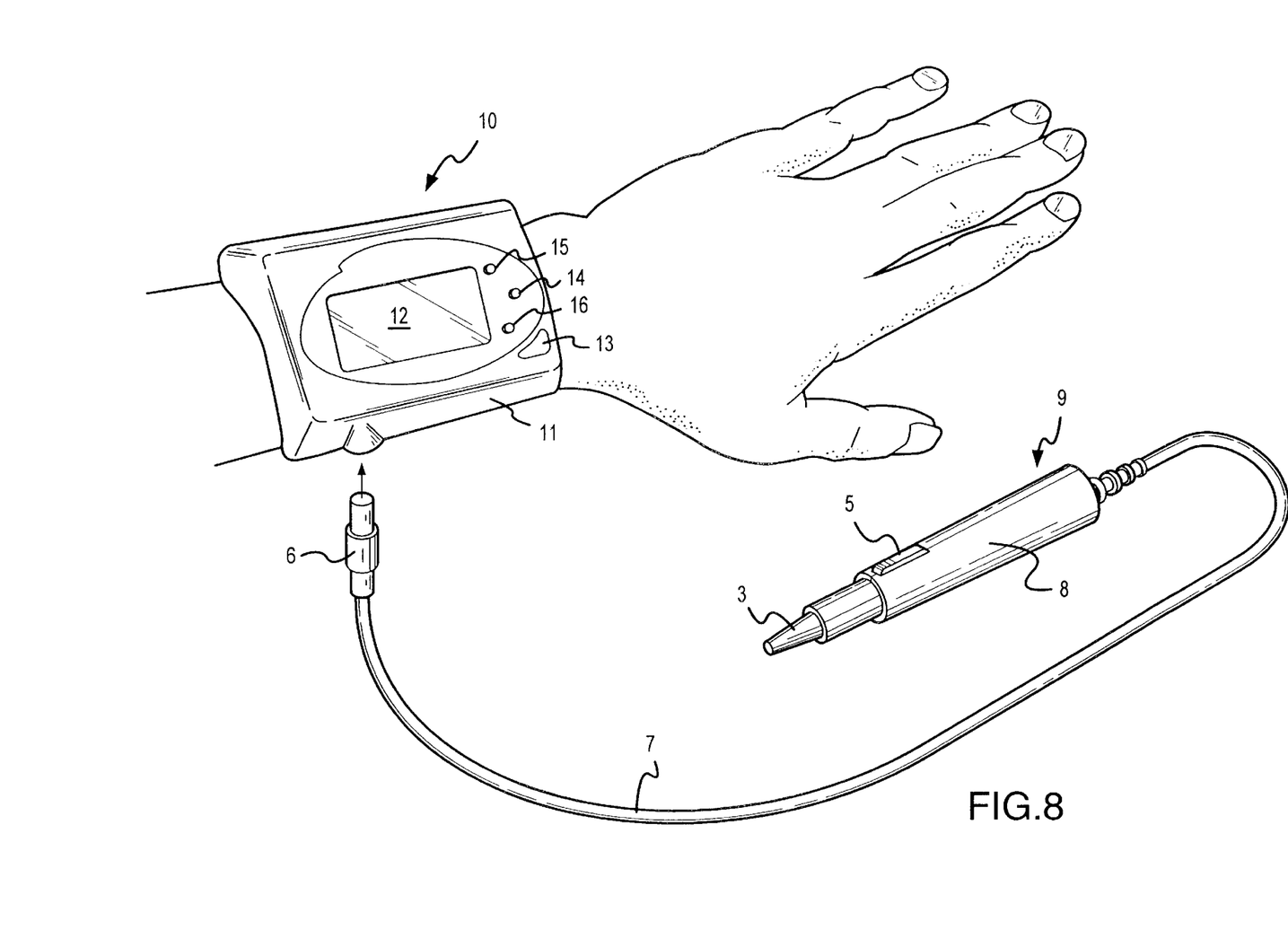
FIG. 8 is a drawing showing the exterior of the modular calorimeter.

An exterior view of a second embodiment of the invention, referred to herein as the modular colorimeter, is shown in FIG. 8. The modular probe 9 comprises modular probe body 8, probe tip 3, measure button 5, cable 7, connector 6, display module 10, modular display panel 12, and control switches coupled to power button 13, menu button 14, scroll up button 15 and scroll down button 16.

The modular calorimeter differs from the calorimeter in that the display, the microprocessor and associated data processing hardware, and the batteries are moved from the body of the colorimeter to a display module. Adding the display module permits the utilization of larger and more comprehensive data processing hardware, a larger display and larger or rechargable batteries. The display module may also include the capability of exchanging data with other devices, such as a computer, via infrared (IR) links, radio frequency (RF) links, cables or other media known in the art.

The modular colorimeter can comprise a cradle (not illustrated) for holding the probe and display module when not in use. The cradle can comprise the data links such as infrared (IR) links, radio frequency (RF) links, cables or other media known in the art for exchanging data with remote devices. It can also provide a battery charger and a calibration reference for the calorimeter.

A set of color values can be translated into a set of coordinates in several accepted color characterization systems. A color value for use in a particular industry could have its coordinate system correlated to color index schemes accepted in that industry. Some such systems are qualitative, such as the color swatch system for characterizing flower colors established by the Royal Horticultural Society. Others are quantitative, such as the x, y, and Y color coordinate system explained in Billmeyer & Saltzman, *Principles of Color Technology* 43 (1966).

Although the invention encompasses monochromatic, discrete-color, and white light sources, emitted colors are referred to as having a nominal wavelengths, and (optionally) some distribution of light intensity at other wavelengths. Various intensity distributions may prove advantageous for a product designer implementing the current invention, depending on component availability or matching to the receptors in the human eye. See, e.g., W. D. Wright, *The Measurement of Color* 69 (1969) for further discussion of this concept. A two-color light source system may be most advantageous for a particular model of probe, based on a designer's empirical knowledge about the intended use: The color of a tooth, for example, can generally be measured adequately by red and yellow light sources.

A database can be used to predict a mixture of ingredients to achieve a desired final color. To accomplish this, color values of a variety of mixtures of pigmented components are stored in the database, which contains information such as ingredient ratios and color values measured before and after curing. By interpolation methods known in the software arts, a computer can use these data to calculate the respective amounts of uncured ingredients and predict the uncured color coordinates of the mixture. The color values of the mixed ingredients can be measured before and after curing, thus serving as a quality control mechanism at several steps in the manufacture of products.

While the invention has been described above with respect to specific embodiments, it will be understood by those of ordinary skill in the art that various changes in form and details may be made therein without departing from the spirit and scope of the invention.

All references mentioned herein are hereby incorporated by reference to the extent that they are not inconsistent with the present disclosure.

What is claimed is:

1. A miniature, self-contained colorimeter, for measuring the color of a target, comprising:
   a body containing:
   a light pipe having an axial bore, a distal end and a proximal end;
   an illumination surface on said distal end;
   a light sensor, aligned with said bore; and
   at least two different-colored light sources, coupled to said proximal end;
   a microprocessor, coupled to said sensor and said sources;
   a display panel, coupled to said microprocessor; and
   a switch, coupled to said microprocessor.

2. A colorimeter as in claim 1 wherein said light sources are LEDs.

3. A calorimeter as in claim 1 wherein said light sources emit red, blue and green light.

4. A colorimeter as in claim 1 wherein said light sources can be sequentially illuminated.

5. A calorimeter as in claim 1 wherein said body has a length not exceeding 150 mm and a cross-sectional area not exceeding 500 $mm^2$.

6. A colorimeter as in claim 1 wherein said switch is contained within said body.

7. A calorimeter as in claim 1 wherein said light sources emit wavelengths which do not overlap.

8. A calorimeter as in claim 1 further comprising an optical filter between said target and said sensor.

9. A colorimeter as in claim 1 further comprising a memory for storing color values.

10. A colorimeter as in claim 1 further comprising a memory for storing computational routines and comparison data.

11. A colorimeter as in claim 1 wherein said display panel is an integral part of said body.

12. A calorimeter as in claim 1 wherein said illumination surface is a diffusing surface.

13. A calorimeter as in claim 1 wherein said illumination surface is a refracting surface.

14. A calorimeter as in claim 1 further comprising a program for computing a ratio of light intensity reflected from a target to light intensity reflected from a substantially white reference.

15. A calorimeter as in claim 14 further comprising a process for comparing said ratio with a stored value.

16. A colorimeter as in claim 1 further comprising a display module containing said microprocessor, said display panel, and a battery for supplying power to said colorimeter.

17. A calorimeter as in claim 1 further comprising a stored calibration routine.

18. A colorimeter as in claim 1 further comprising a stored measurement routine.

19. A colorimeter as in claim 1 further comprising a stored comparison routine.

20. A calorimeter as in claim 11 wherein said body contains said microprocessor, said switch, and a battery.

21. A colorimeter as in claim 1 further comprising an optical filter for shielding said sensor from undesired wavelengths.

22. A calorimeter as in claim 1 further comprising a notch filter for shielding said sensor from overlapping wavelengths emitted by said light sources.

23. A calorimeter as in claim 1 wherein said colorimeter includes a threshold process for eliminating overlapping wavelengths emitted by said light sources.

24. A calorimeter as in claim 16 further comprising a battery contained within said display module.

25. A colorimeter as in claim 16 further comprising a wrist strap attached to said display module.

26. A colorimeter as in claim 16 further comprising a link for exchanging data with a computer.

27. A calorimeter as in claim 1 further comprising a removable probe tip.

28. A calorimeter as in claim 1 further comprising a disposable probe tip.

29. A colorimeter as in claim 1 further comprising a control switch in said display module.

30. A method, for measuring the color of a target, comprising the steps of:
   providing a miniature, self-contained calorimeter, comprising:
      a body containing:
         a light pipe having an axial bore, a distal end and a proximal end;
         an illumination surface on said distal end;
         a light sensor, aligned with said bore; and
         at least two different-colored light sources, coupled to said proximal end;
      a microprocessor, coupled to said sensor and said sources;
      a display panel, coupled to said microprocessor; and
      a switch, coupled to said microprocessor;
   sequentially illuminating a reference target with a plurality of colors;
   measuring the light reflected from the reference target for each of the colors;
   generating and storing a reference value representing the light measured for each of the colors;
   sequentially illuminating the target with a plurality of colors;
   measuring the light reflected from the target for each of the colors;
   generating and storing a color value representing the light measured for each of the colors; and
   computing a ratio of each color value to each reference value.

31. A method as in claim 30 further comprising the step of:
   displaying a symbol representing each ratio on the display panel.

32. A method as in claim 30 further comprising the steps of:
   comparing each ratio with a stored ratio; and
   displaying a symbol representing a result of each comparison on the display panel.

* * * * *